United States Patent
Morad et al.

(10) Patent No.: US 11,576,828 B2
(45) Date of Patent: *Feb. 14, 2023

(54) APPARATUS TO DISPENSE FEMININE HYGIENE PRODUCTS WITH ONE OR MORE USER SENSORS

(71) Applicant: TRANZONIC COMPANIES, Cleveland, OH (US)

(72) Inventors: Fred I. Morad, Toluca Lake, CA (US); Robert A. Acosta, Norwalk, CA (US)

(73) Assignee: TRANZONIC COMPANIES, Cleveland, OH (US)

(*) Notice: Subject to any disclaimer, the term of this patent is extended or adjusted under 35 U.S.C. 154(b) by 0 days.

This patent is subject to a terminal disclaimer.

(21) Appl. No.: 17/947,330

(22) Filed: Sep. 19, 2022

(65) Prior Publication Data

US 2023/0017187 A1    Jan. 19, 2023

Related U.S. Application Data

(63) Continuation of application No. 16/550,422, filed on Aug. 26, 2019, now Pat. No. 11,446,188.

(Continued)

(51) Int. Cl.
*B25J 13/08* (2006.01)
*A61F 15/00* (2006.01)
*G06F 3/0488* (2022.01)

(52) U.S. Cl.
CPC .......... *A61F 15/003* (2013.01); *G06F 3/0488* (2013.01); *B25J 13/086* (2013.01)

(58) Field of Classification Search
CPC ................. A61F 15/001; A61F 15/003; A61F 13/55135; A61F 13/55175; G06F 3/0488; B25J 13/086; G07F 11/045; G07F 11/10; G07F 11/22; G07F 17/0092; G07F 17/18; G07F 5/02; G07F 9/04; G08B 21/18; G08B 21/182

See application file for complete search history.

(56) References Cited

U.S. PATENT DOCUMENTS 9,501,888 B1 * 11/2016 Morad .................. G07F 11/10
9,721,419 B1 *  8/2017 Morad .................. A61F 15/003

(Continued)

OTHER PUBLICATIONS

Wan et al., Human-subject tracking and localization fora hand hygiene monitoring system, 2015, IEEE, p. 128-132 (Year: 2015).*

(Continued)

*Primary Examiner* — Mcdieunel Marc
(74) *Attorney, Agent, or Firm* — Taft Stettinius & Hollister LLP; Ryan O. White; Daniel J. Krieger

(57) ABSTRACT

A dispenser of feminine pads and tampons activated by a touch sensor or a proximity sensor. The touch of or the proximity of a person's hand closes an electronic circuit causing a motor to rotate. The motor is attached to a shaft which rotates. The shaft retains a feminine product dispenser. The feminine product dispenser transports a feminine napkin or tampon to a retrieval tray. The improved design enables the sanitary napkin rail and tampon rail to be adjacent to each other, thereby reducing the width requirements for the cabinet housing the rails. The activation by a touch screen or a proximity sensor significantly improves the selection and dispensing of the desired feminine napkin product and tampon product.

20 Claims, 12 Drawing Sheets

Related U.S. Application Data

(60) Provisional application No. 62/723,278, filed on Aug. 27, 2018.

(56) References Cited

U.S. PATENT DOCUMENTS

| | | | |
|---|---|---|---|
| 10,937,268 B1* | 3/2021 | Morad | A61F 13/5519 |
| 11,141,328 B1* | 10/2021 | Morad | A61F 15/001 |
| 11,446,188 B2* | 9/2022 | Morad | G06F 3/0488 |
| 2019/0105211 A1* | 4/2019 | Morad | G07F 11/045 |
| 2019/0240089 A1* | 8/2019 | Merry del Val | G07F 11/004 |
| 2020/0005580 A1* | 1/2020 | Morad | G08B 21/18 |
| 2021/0267823 A1* | 9/2021 | Loffredo | G07F 17/0092 |

OTHER PUBLICATIONS

Shankaraiah et al., Android based fluid dispensing and blending system automation, 2014, IEEE, p. 1-5 (Year: 2014).*

Sheng et al., Sustainable development with green productivity in manufacturing, 2005, IEEE, p. 267-270 (Year: 2005).*

\* cited by examiner

APPARATUS TO DISPENSE FEMININE HYGIENE PRODUCTS WITH ONE OR MORE USER SENSORS

RELATED APPLICATION

This application is a continuation patent application of U.S. patent application Ser. No. 16/550,422, entitled "An Apparatus to Dispense Feminine Hygiene Products With One or More User Sensors" which claims priority to U.S. Provisional Patent Application Ser. No. 62/723,278 entitled "Apparatus to Dispense Feminine Hygiene Products Through Touch Screen Sensors, the Apparatus Including a Time Delay Function", filed Aug. 27, 2018, the disclosures of which are each incorporated by reference herein in their entirety.

FIELD OF THE DISCLOSURE

The present disclosure relates to vending machines that dispense hygiene products. More specifically, the present disclosure relates to vending machines that dispense feminine hygiene products without requiring any physical activity of turning a knob or other physical apparatus to dispense the feminine hygiene products from the vending a machine. Additionally, vending machines that dispense feminine hygiene products that do not require depositing any coins or any other compensation to receive the feminine hygiene products are described.

BACKGROUND OF THE DISCLOSURE

The closest prior art of which the present inventors are aware include the following: (1) U.S. Pat. No. 9,721,419 for "Vending Machine for Retaining and Dispensing Feminine Hygiene Products Through a Novel Coin Operating Apparatus"; (2) U.S. Pat. No. 9,501,888 for "Vending Machine for Retaining and Dispensing Feminine Hygiene Products Through a Novel Coin Operating Apparatus"; and (3) U.S. Pat. No. 10,192,386 for "Mechanical Time Delay Product Dispenser".

U.S. Pat. Nos. 9,721,419, 9,501,888, and 10,192,386 have the same co-inventors as the present application (Fred I. Morad and Robert A. Acosta).

SUMMARY

The present invention includes a vending machine which contains two rows of feminine hygiene products adjacent one another, with sanitary pads in one row and tampons in a second row. Other types of hygiene products and vending machines therefore are contemplated, such as hygiene products for men. The products are aligned in rails, one above the other within the row, and there is a weight on top of each row of the products to create a downward force to enable the next successive product to be placed in condition for dispensing after the lowermost product has been dispensed. The rails have a rear surface and a pair of side rails which envelope the specific packaging in which each respective feminine hygiene product is retained. There is an aligned horizontal dispensing platform on which the lowest feminine hygiene product is retained with opposite distribution arms which assist in dispensing the retained lowermost feminine hygiene product and assist in receiving the next lowermost feminine hygiene product. Each pair of distribution arm receives the lowermost feminine napkin or tampon and rotates in one direction by about 45 degrees to enable the product to be dispensed into a retrieving tray. The dispensing arms then reverse direction and rotate backwards by about 45 degrees and are stopped by a limit switch when they return to their initial position.

The operation of the vending machine is controlled by a computer chip in the motherboard. A left touch sensor, also referred to as a feminine napkin or feminine pad touch sensor, is affixed to the rear of the front door and in one embodiment includes four wire leads which are connected to respective female connectors on the motherboard. A right touch sensor, also referred to as a tampon touch sensor, is also affixed to the rear of the front door and is connected, in one embodiment, by four wire leads to female connectors on the motherboard. A power pack which is battery pack which, by way of example, includes four "AA" batteries, is hardwired, in one embodiment by two wiring leads from the battery pack to female connectors on the motherboard. A door switch which is at the lower portion of the door is also hardwired to female connectors on the motherboard, in one embodiment, by a pair of wire leads. A feminine napkin drive motor is hardwired to the motherboard, in one embodiment, by two wire leads from the left motor or feminine napkin motor to female connectors on the motherboard. A left micro-switch with a spring steel extension is also hardwired, in one embodiment, by two hard wire leads to female connectors on the motherboard. A left reed switch or feminine napkin reed switch is also hardwired to female connectors to the motherboard. In other embodiments, a proximity sensor is contemplated for one or both of the left touch sensor and the right touch sensor. As further described herein, a discussion directed to a touch sensor also includes the use of a proximity sensor.

The feminine napkins are retained in a rail in a vertically aligned row of products with a weight thereon and a magnet on top of the weight. When the supply of feminine napkins is exhausted and there are no more feminine napkins in the row, the magnet on top of a weight at the top of the feminine napkin column touches the left reed switch or feminine napkin reed switch which causes a warning light to blink on and off. The warning light includes one or more variations. As shown in the Figures which will be described, the left warning light or feminine napkin warning light is hardwired, in one embodiment, by two wire leads to female connectors on the motherboard. Therefore, when the rail retaining the column of feminine napkins is out of feminine napkins, the magnet on top of the weight comes in contact (either by magnetic contact or direct contact) with the reed switch at the bottom of the feminine napkin column and the light blinks on and off and is visible through an opening in the front door. The opening, in one embodiment, is at a location where a symbol (not shown) for the feminine napkin is located on the front door. In an alternative variation, the light is incorporated into a touch sensor board of the feminine napkin product and the light also shines through an opening in the front door and blinks on and off to show that the machine is out of this product. In other embodiments, the magnet is located at positions other than the top of the weight.

Also when a touch sensor is touched, this causes the feminine napkin motor shaft to rotate three-hundred sixty degrees which in turn is connected to a flywheel which also rotates three-hundred sixty degrees which in turn is connected to a crank arm which moves in the generally vertical direction which is in turn connected to a cradle. The cradle rotates forty-five degrees in one direction to cause the feminine napkin product to fall into a dispensing tray and then the cradle rotates in the reverse direction back to its original position and is stopped by a limit switch. After rotation, a spring steel extension from the limit switch touches the cradle and causes it to stop rotation. The cradles are ready to receive the next lowest feminine napkin package.

With respect to the tampons, the tampon motor or right motor is hardwired, in one embodiment, by two wire leads to the female connectors on the motherboard. A right limit switch or tampon limit switch is hardwired, in one embodiment, by two wire leads connected to the female connectors on the motherboard. A second rail which retains a column of tampons also has a weight on the column of tampons and a magnet on the weight. When a touch sensor is touched, this causes activation through the tampon sensor. The operation of the vending machine is controlled by a computer chip in the motherboard. The right touch sensor, also referred to as a tampon sensor, is affixed to the rear of the front door and contains, in one embodiment, three wire leads which are connected to respective female connectors on the motherboard. A tampon drive motor is hardwired to the motherboard, in one embodiment, by two wire leads from the right motor or tampon motor to female connectors on the motherboard. A right micro-switch with a spring steel extension is also hardwired, in one embodiment, by two hard wire leads to female connectors on the motherboard. A right reed switch or tampon reed switch is also hardwired to female connectors to the motherboard.

The tampons are retained in a rail in a vertically aligned row of products with a weight thereon and a magnet located at or on top of the weight. When the supply of tampons is exhausted and there are no more tampons in the row, the magnet at the top of weight on the tampon column touches the right reed switch or tampon reed switch which causes a warning light to blink on and off. The warning light includes have one or more variations. As shown in the Figures which will be described, the right warning light or tampon warning light is hardwired, in one embodiment, by two wire leads to female connectors on the motherboard. Therefore, when the rail retaining the column of tampons is out of tampons, the magnet on top of the weight comes in contact (either by magnetic contact or direct contact) with the reed switch at the bottom of the tampon column and the light blinks on and off and is visible through an opening in the front door. The opening is at a location where a symbol (not shown) for the tampon is located on the front door. In an alternative variation, the light is incorporated into the touch sensor board of the tampon product and the light also shines through an opening in the front door and blinks on and off to show that the machine is out of this product.

Also when a touch sensor is touched, this causes the tampon motor shaft to rotate three-hundred sixty degrees which in turn is connected to a flywheel which also rotates three-hundred sixty degrees which in turn is connected to a crank arm which moves in the vertical direction which is in turn connected to cradle. The cradle rotates forty-five degrees in one direction to cause the tampon product to fall into a dispensing tray and then the cradle rotates in the reverse direction back to its original position and is stopped by a limit switch. After rotation, a spring steel extension from the limit switch touches the cradle and causes it to stop rotation. The cradles are ready to receive the next lowest tampon package.

All of this is controlled by the computer chip in the motherboard. Built into the computer is a time delay so that someone cannot empty the machine by continuously touching the touch sensor for dispensing either feminine napkins or tampons. Once a product such as a feminine napkin is dispensed, the computer program causes a time delay of about 5 seconds. In other embodiments, other time delays are contemplated including time delays of anywhere from two seconds to ten seconds before either another feminine napkin or a tampon is dispensed. Therefore, the time delay causes an ability to immediately inactivate the machine to dispense a second product and the time delay prevents someone from continuously activating the touch sensor to dispense all of the products in the machine. The time delay works both ways for both products. If a tampon is dispensed, then the time delay prevents a second tampon or a first feminine napkin from being dispensed until the computer set time such as two seconds to thirty seconds has elapsed.

There are one or more touch sensors or one or more motion sensors in different embodiments. If a touch sensor is activated, there is a time delay of about two seconds such that a second hygiene product is not dispensed if the touch sensor is activated before the time delay of two seconds has elapsed. If a motion sensor is activated, there is a time delay of about five seconds such that a second hygiene product is not dispensed if the motion sensor is activated before the time delay of 5 seconds has elapsed. Other time delays for both the touch sensor and the motion sensor are contemplated.

Touching the left sensor activates the sensor to close an electronic circuit. When the electronic circuit is closed, a motor is activated. The motor includes a motor shaft connected to a flywheel which is connected to a crank arm which is operatively connected to a cradle or to a feminine hygiene product dispensing member (such as a double tooth dispenser). The motor causes the shaft to rotate. The shaft drives the cradle that supports the feminine hygiene product, which by way of example, is a cradle having dispensing arms. Upon activation, the cradle rotates about forty-five degrees in a first direction to enable the feminine napkin to fall off the cradle and into a dispensing/receiving tray. The cradle continuously is in motion and after the product is dispensed, rotates forty-five degrees in a second direction opposite the first direction until the cradle returns to its initial position to receive the next feminine hygiene product such as a feminine napkin. As described herein, the first direction is a direction towards the back of the machine and away from a user standing in front of the apparatus. The second direction is a direction toward the front of the machine and toward the user standing in the front of the apparatus. Consequently, the first direction is also considered to be a forward direction (away from the user and toward the back wall) and the second direction is considered to be a backward direction (toward the user toward the front wall) with respect.

Touching the right sensor activates the sensor to close an electronic circuit. When the electronic circuit is closed, a motor is activated. The motor is connected to a shaft which retains a tampon product dispensing member. The motor causes the shaft to rotate. The shaft retains the tampon product receiving/retaining and dispensing member, which by way of example, is a tray bounded by dispensing arms. The receiving tray includes a horizontal receiving tray and oppositely disposed arms. Upon activation, the feminine hygiene product receiving/retaining and dispensing member rotates about forty-five degrees in the forward direction to enable the tampon to fall off the tray and into a dispensing/ receiving tray. The feminine hygiene product receiving/ retaining and dispensing member is in continuous motion and after a tampon is dispensed, then rotates in the opposite backward direction by forty-five degrees until it rotates back to its initial position and is ready receive the next in a row tampon.

Once in the receiving tray, the feminine hygiene product is retrieved by a person's hand. When the product dispensing member is returned to its initial starting position after the rotation, the apparatus is off until a touch sensor is activated to begin the cycle again. The weight on top of the column causes the second lowermost product in the column to become the lowermost feminine hygiene product which falls onto the second horizontal receiving tray.

In one embodiment, there is one electronic assembly for each product. There is one circuit board and one set of connectors with connecting wires for the sanitary pads. There is a second separate circuit board and second set of connectors with connecting wires for the tampons.

It is also within the spirit and scope of the present disclosure to have one circuit board (also called a motherboard) as disclosed herein which is hardwired to two separate sensors, one for activating and dispensing a sanitary pad, interchangeably referred to herein as a sanitary napkin, and a second for activating and dispensing a tampon. In one or more embodiments disclosed herein, the retaining elements described in the above paragraph are incorporated in one circuit board (also called the motherboard) with the circuit board configured to send an appropriate product related signal when an associated sensor is triggered.

The present apparatus includes a housing of a plastic or other comparable container with a cover made of different materials and preferably opaque. The cover cannot be made of material which interferes with the sensor's ability to receive and detect touch to activate the touch sensor. The cover cannot be made of material that interferes with the touch activity detectable by the touch sensor. Therefore, in one embodiment there is provided a vending machine with a cover which conceals the circuit boards and sensors on the back of the cover for both the dispensing of sanitary pads and tampons which facilitates the transmission of signals through a printed circuit board to carry out the signals as described above to cause the activation by hand signal.

In another embodiment, a dispenser dispenses feminine hygiene products including sanitary napkins and tampons by a simple hand touch without requiring any physical action on the part of the person such as placing coins in the machine or rotating a handle or performing any other comparable physical activity. While such activities may be simple for younger and healthier people, as the population ages, it is more difficult for older people to do the simplest tasks such as rotating a heavy handle or placing the right amount of coins inside a machine. Therefore, by not having to do anything other than touch the appropriate sensor, the difficulty in obtaining a sanitary pad or tampon is substantially reduced.

In one embodiment, there is provided a dispensing apparatus for dispensing hygiene products. The apparatus includes a first hygiene product rail having a first sidewall, wherein the first hygiene product rail is adapted to hold first hygiene products, and a second hygiene product rail. The second hygiene product rail includes a second sidewall adapted to hold second hygiene products. The apparatus further includes a motherboard and a first hygiene product sensor operatively connected to the motherboard, wherein activation of the first hygiene product sensor dispenses first hygiene products from the first hygiene product rail. A second hygiene product sensor is operatively connected to the motherboard, wherein activation of the second hygiene product sensor dispenses second hygiene products from the second hygiene product rail.

In an additional embodiment there is provided a hygiene product dispensing apparatus for dispensing hygiene products including a first hygiene product structure having a first sidewall, wherein the first hygiene product structure to hold first hygiene products, and a second hygiene product structure having a second sidewall, the second hygiene product structure to hold second hygiene products. The apparatus further includes a computer chip and a first hygiene product sensor operatively connected to the computer chip, wherein activation of the first hygiene product sensor dispenses first hygiene products from the first hygiene product structure. a second hygiene product sensor is operatively connected to the computer chip, wherein activation of the second hygiene product sensor dispenses second hygiene products from the second hygiene product structure. The computer chip is programmed to include a time delay and if one of the first hygiene product or the second hygiene product products is dispensed, the computer chip provides an automatic time delay before the other of the first hygiene product or the second hygiene product is dispensed.

In a further embodiment, there is provided a method of dispensing a first hygiene product and a second hygiene product from a dispensing apparatus. The method includes providing a first hygiene product rail to hold a first column of a plurality of the first hygiene products; providing a second hygiene product rail to hold a second column of a plurality of the second hygiene products; dispensing one of the plurality of first hygiene products from the first column in response to activation of a first sensor, wherein the response is based on a condition of a switch having a touch activation mode or a proximity activation mode; dispensing one of the second hygiene products from the second column in response to activation of a second sensor, wherein the response is based on the condition of the switch having the touch activation mode or the proximity activation mode; and illuminating a light if one of the first column or the second column is out of the first hygiene product or second hygiene product.

Further novel features and other aspects of the present invention will become apparent from the following detailed description and discussion.

BRIEF DESCRIPTION OF THE DRAWINGS

Referring particularly to the drawings for the purpose of illustration only and not limitation, there is illustrated.

DETAILED DESCRIPTION OF THE EMBODIMENTS

Although specific embodiments of the present invention will now be described with reference to the drawings, it should be understood that such embodiments are by way of example only and merely illustrative of but a small number of the many possible specific embodiments which can represent applications of the principles of the present invention. Various changes and modifications obvious to one skilled in the art to which the present invention pertains are deemed to be within the spirit, scope and contemplation of the present invention.

Figure 12:
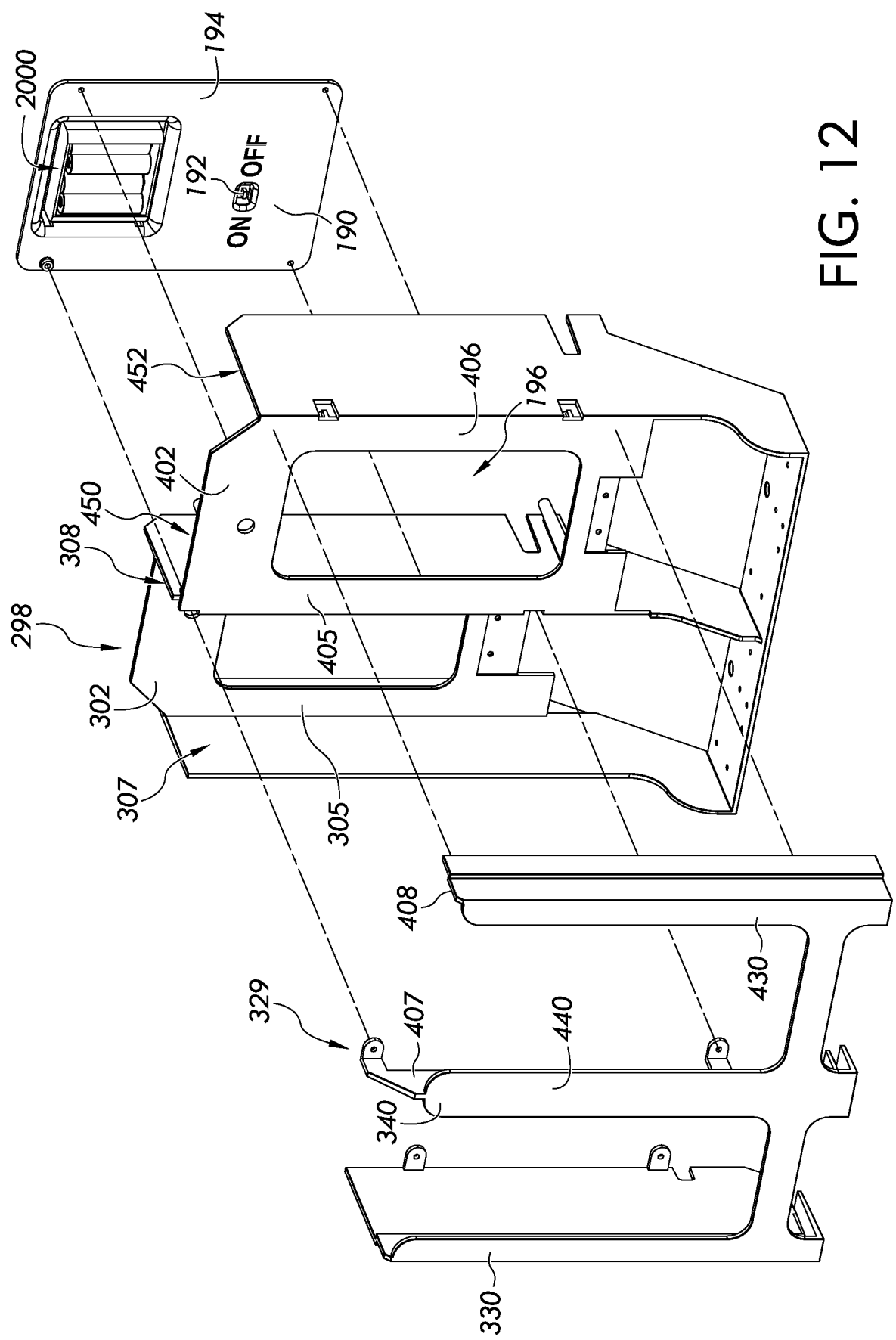
FIG. 12 is an exploded perspective view of a portion of the dispenser apparatus.

Referring to FIGS. 1 through 5, there is illustrated a feminine hygiene product dispensing apparatus 10. The apparatus 10 includes a front door 20, the front door 20 having a back wall 30 with a rear surface 32. The front door 20 is illustrated in dotted outline to illustrate different components, parts, and devices that would otherwise be hidden from view. The front door 20 is hinged to a lower portion 22 of a housing 24. The apparatus 10 includes the housing 24 having a back wall 70, two sidewalls 72 and 74, a top wall 76 that is part of the door 20, and a bottom wall 78 which surrounds an interior chamber 80. A back module 298 (see FIG. 12) includes two rails; a first rail 322 having a back wall 302, a pair of longitudinal back walls 305 and 306 (see FIG. 1) extending to a pair of longitudinal sidewalls 307 and 308 which extend to a front module 329 which includes a pair of longitudinal front walls 330 and 340 to retain a vertically aligned column/stack of sanitary pads (alternatively called "sanitary napkins"). In the illustrated embodiment of FIG. 12, the back module 298 is a single unitary part. In other embodiments, the back module 298 is formed of multiple parts.

A second rail 422 (see FIG. 1) is adjacent to the first rail, the second rail also having a back wall 402, a pair of longitudinal back walls extending to a pair of longitudinal sidewalls which extend to a pair of longitudinal front walls to retain a vertically aligned column/stack of tampons. The first rail is deeper than the second rail. The first rail retains the sanitary napkins. The second rail retains the tampons. For each rail, there is an aligned horizontal dispensing platform on which the lowest feminine hygiene product is retained with opposite blocking members which assist in dispensing the retained lowermost feminine hygiene product and assist in receiving the next lowermost feminine hygiene product on the same dispensing platform. Each column further includes a top weight bearing platform thereon which forces the second lowermost feminine hygiene product onto the receiving platform after the lowermost feminine hygiene product has been dispensed into a receiving tray. For each column, the weight includes a magnet which comes generates an electronic signal to illuminate a light if a column of the sanitary hygiene products or tampon products is out of product.

Each column/stack operates independently of the other. The first rail 322 retains a column 300 of sanitary pads 3000. The first rail 322 which retains the sanitary napkins 3000 has a back wall 302 with respective longitudinal back walls 305 and 306 extending to respective longitudinal sidewalls 307 and 308 which in turn are attached to respective longitudinally attached transversely extending front walls 330 and 340 to create a frame. The sidewalls 307 and 308 are part of the back module 298. (See FIGS. 1 and 12)

Spaced apart and parallel to retaining the column 300 of sanitary pads 3000, there is a second rail 422 retaining a column/stack 400 of tampons 4000. The second rail 422 which retains the tampons 4000 has a back wall 402 with respective longitudinal back walls 405 and 406 extending to respective longitudinal sidewalls 407 and 408 which in turn are attached to respective longitudinally attached transversely extending front walls 430 and 440 to create a frame. The front module 329 forms the sidewalls 407 and 408. Sidewalls 308 and 407 are adjacent to each other and are formed by the front module 329. In the illustrated embodiment, the front module 329 is a single unitary part. In other embodiments the front module is formed by multiple parts. In one example the multiple parts forming the front module 329 are situated side by side such that side walls 308 and 407 are separated with only a small gap between them. This results in a compact apparatus or feminine hygiene product vending machine.

The front module 329 when attached to the back module 298 forms the sanitary pad rail 300 and the tampon rail 400. The back module 298 further includes a first back side wall 450 and a second back sidewall 452 disposed on either side of surface 454 of the back wall 402. The surface 454 receives the power pack 2000 and further includes a portion to which the motherboard 1000 is connected. By locating both the power pack 2000 and the motherboard 1000 on the back side of the back wall 402, both of the rails 300 and 400 are separated by only by the material forming the walls 308 and 450. With this structure, the illustrated embodiment provides a compact and efficient structure.

Further referring to FIGS. 1 through 5, there is illustrated the dispenser apparatus 10 which contains all of the components previously described and to a left side, the rotatable front door 20 with a back wall 30 having a rear surface 32. The two sensor boards respectively include a respective sensing apparatus which is connected to a motherboard 1000 which controls the operation of the apparatus and which motherboard in turn is electrically connected to an operating mechanism for dispensing the products. The motherboard 1000 has a multiplicity of female plugs or connectors. Three wire leads from each sensor are respectively connected to the three respective connectors on the motherboard.

Thereafter, two wire leads are respectively connected to other components as will be described. While wire leads are described herein as having a specific number of wires, other embodiments having other numbers of leads are contemplated.

There is a first touch sensor circuit board 130 which contains therein a first touch sensor 132 which is a feminine napkin sensor which is hardwired by wire leads 130WL which is a four ribbon wire to respective female connectors on the motherboard, also called contact distribution board or circuit board 1000. Wire leads 120WB are hardwired from two respective female connectors on the motherboard 1000 to the source of power 2000, which by way of example, is a battery pack with four (4) double "AA" batteries, or cell type batteries. The motherboard 1000 is also hardwired by a portion of a four wire ribbon with two wire leads 140WL from female connectors on the motherboard 1000 to first micro limit switch 140 and two wire leads 160WL from female connectors on the motherboard 1000 to a first or left driver motor 160. The left driver motor 160 is connected to a first shaft 162.

There is a second sensor circuit board 230 which is a tampon sensor board which contains therein a second sensor 232 which is hardwired by wire leads 230WB which is a four ribbon wire to respective female connectors on motherboard, also called contact distribution board or circuit board 1000. The motherboard 1000 is also hardwired by a portion of a four wire ribbon with two wire leads 240WR from female connectors on the motherboard 1000 to a second micro limit switch 240 and to two wire leads 260WL from female connectors on the motherboard 1000 to second or right driver motor 260. The second driver motor 260 is connected to a second shaft 262. In other embodiments, one or both of the sensors 132 and 232 are proximity sensors activated by the proximity of a person. In one embodiment, one or both of the sensors are activated by a person's hand that is close to the proximity sensors but is not in contact with the sensor.

The power pack 2000, which in the embodiment shown, contains four "AA" batteries. It will be appreciated that any other type of power pack running on any other type of batteries would also be within the spirit and scope of the present invention. Other types of power supplies are contemplated including connection of the dispenser apparatus to a building's electrical power system. In different embodiments, the connection to the building power system is made by plugging a power cord into a wall outlet or hardwiring the dispenser apparatus to the building power system.

A left reed switch 31ORS is hardwired by two wires to connectors on the motherboard. A right reed switch 41ORS is hardwired by two wires to connectors on the motherboard.

Figure 3:
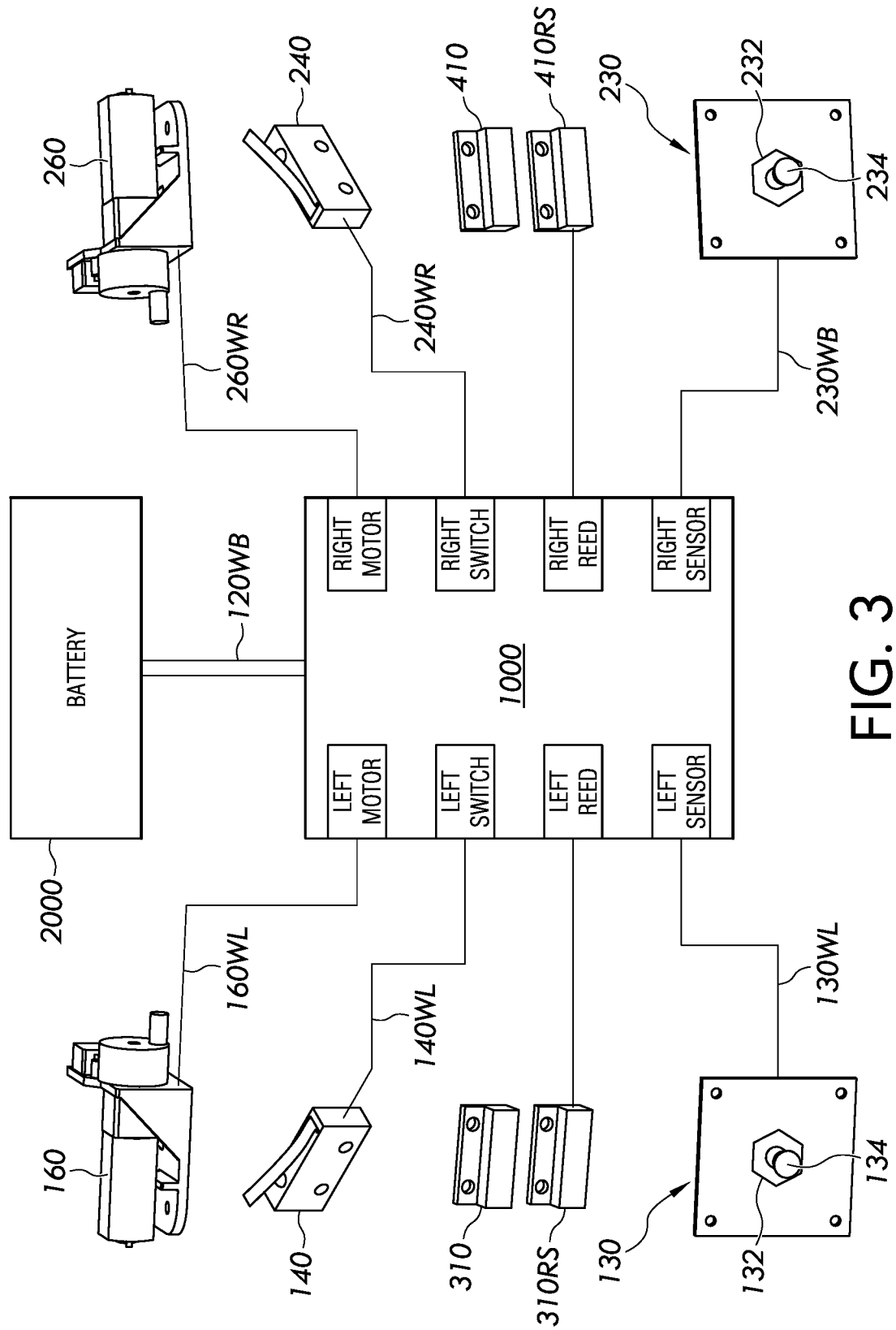
FIG. 3 is a wiring diagram of a motherboard and a components hardwired by wire leads to female connectors on the motherboard.
Figure 4:
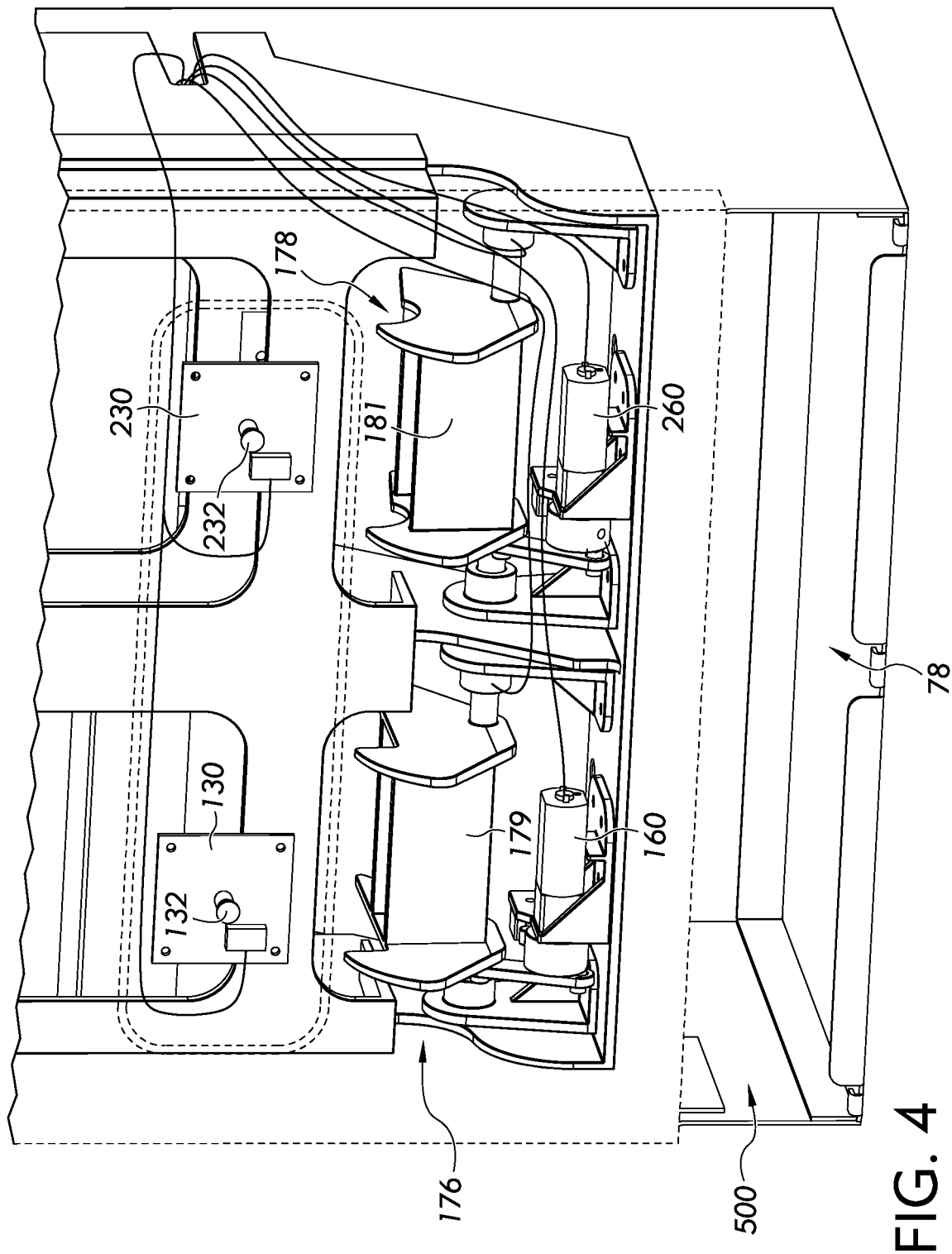
FIG. 4 illustrates an internal perspective front view of the lower portion of a dispenser apparatus.
Figure 5:
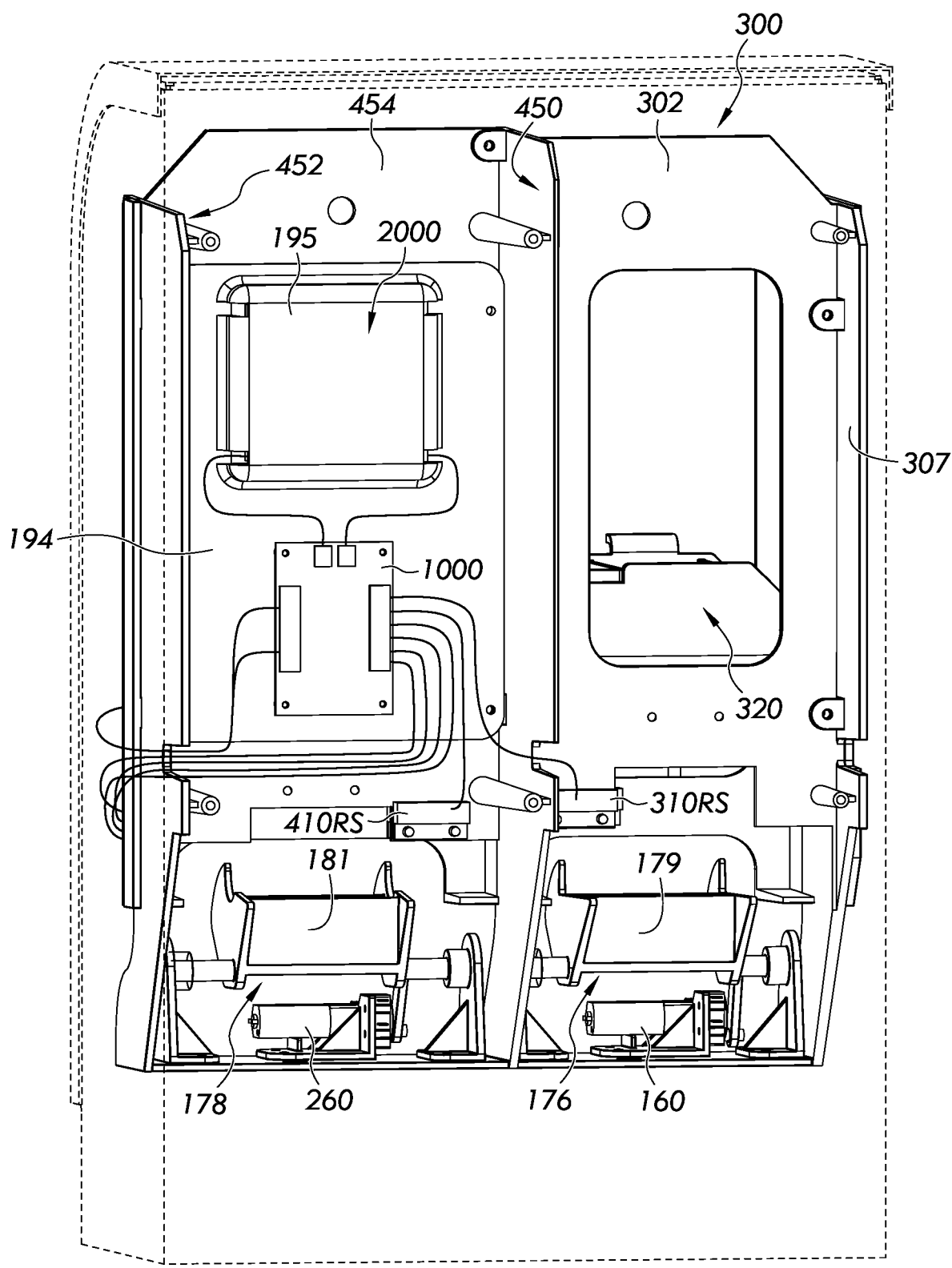
FIG. 5 illustrates a back view of the of the dispenser apparatus.
Figure 6:
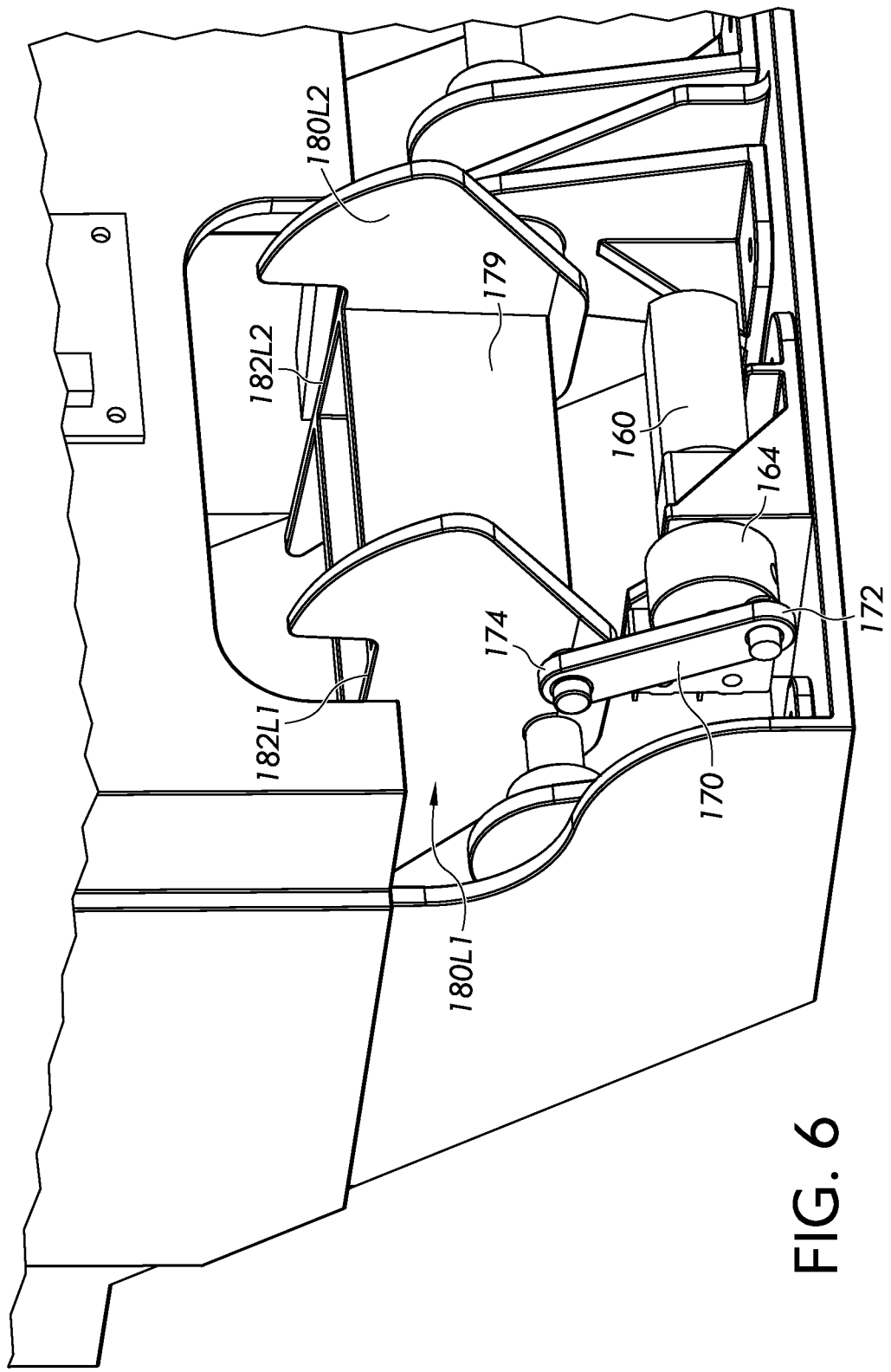
FIG. 6 illustrates a close-up view of the motor and the connection between the motor, the rotating flywheel, the crank arm and the dispensing arm for the sanitary napkin operating mechanism.
Figure 7:
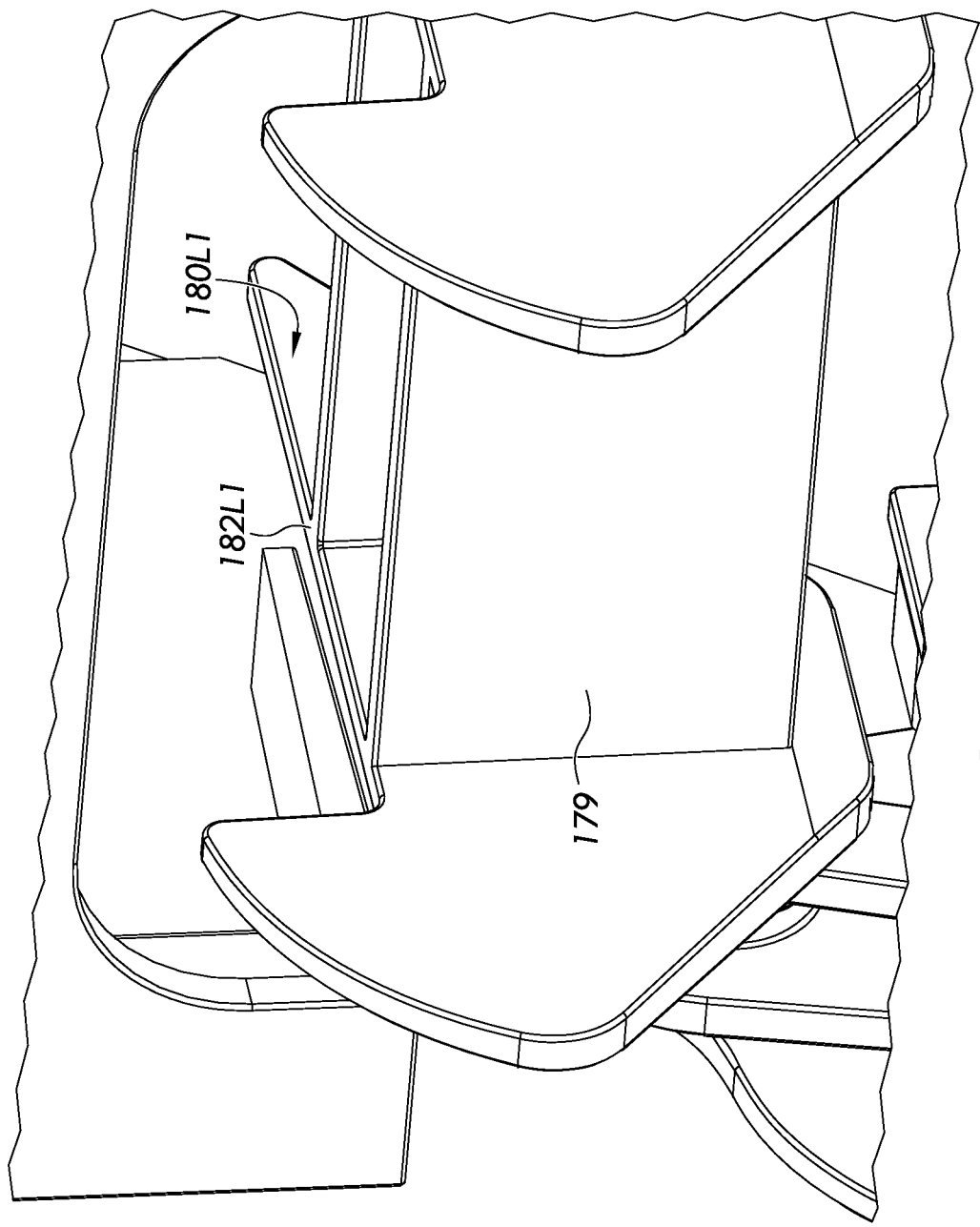
FIG. 7 illustrates a close-up view of one of the dispensing arms for the sanitary napkin dispenser.
Figure 8:
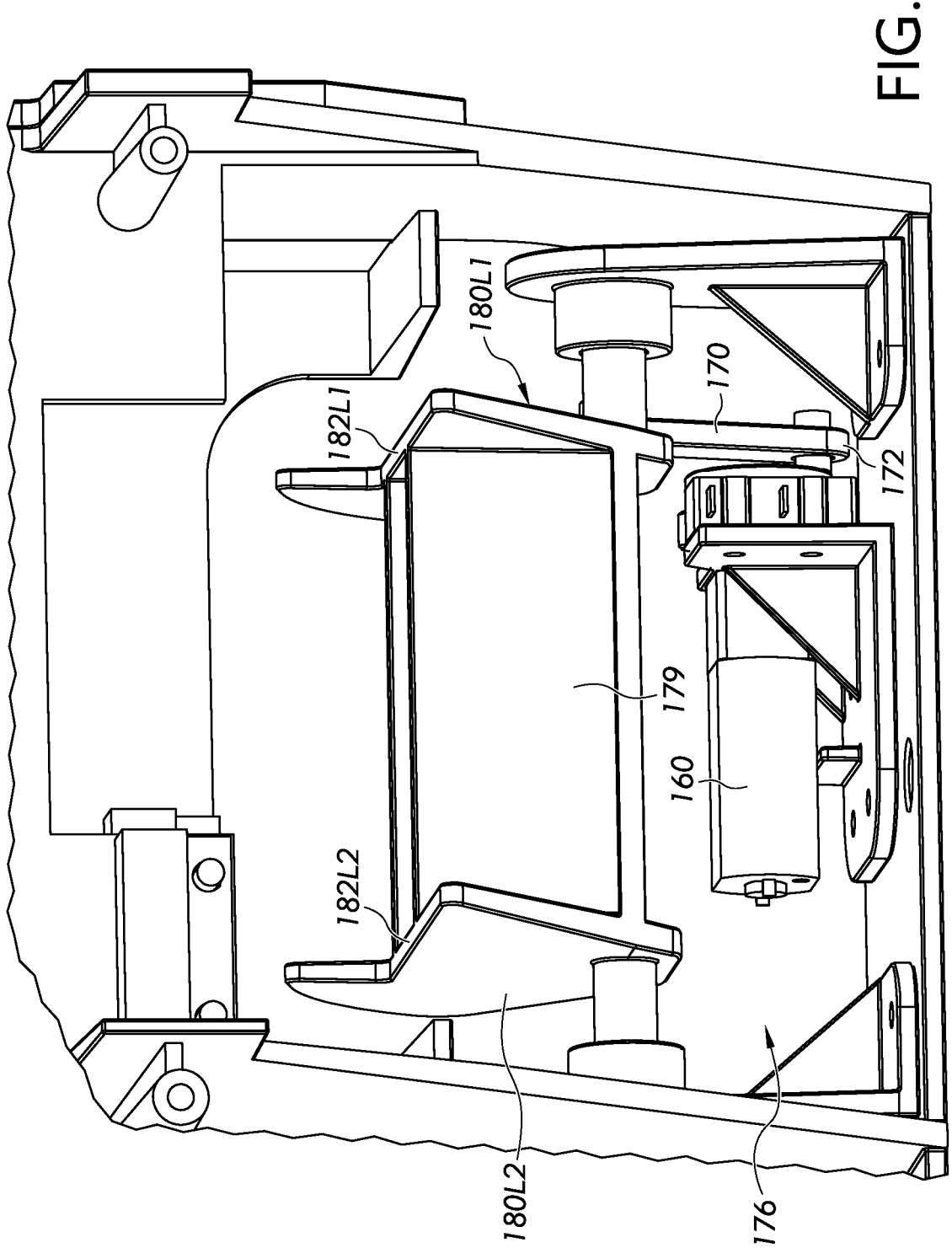
FIG. 8 illustrates a close-up view of both dispensing arms in the initial resting position for the sanitary napkin dispenser.
Figure 9:
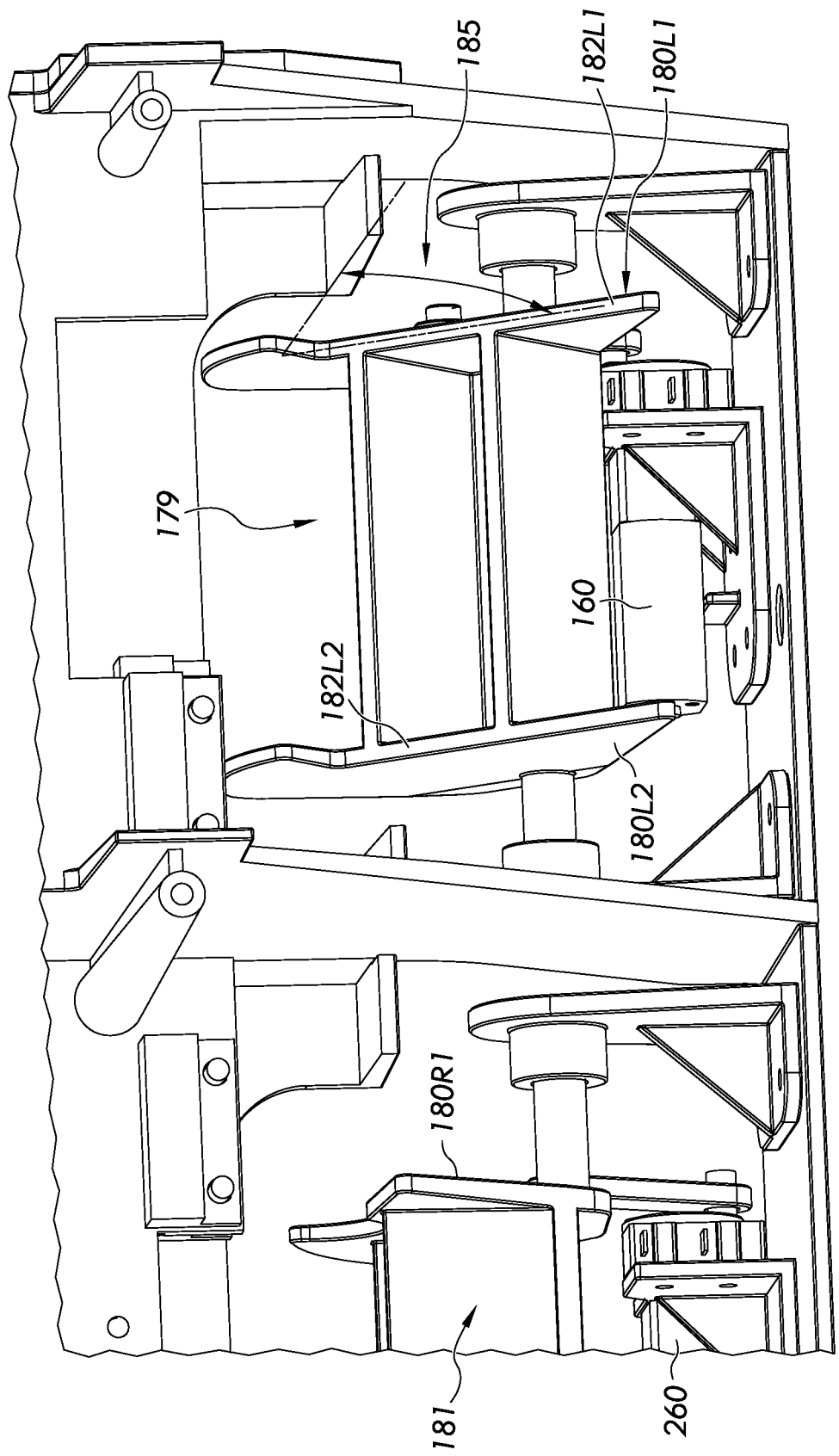
FIG. 9 illustrates a close-up view of both dispensing arms in the forward position for the sanitary napkin dispenser.

There are two or more alternative variations for the signaling light. Referring to FIG. 3, there is also a signaling light 134 which is a red LED light on sensor board 130 and a signaling light 234 which is a red LED light on sensor board 230. Signaling light 134 blinks on and off when the feminine napkin rail is out of feminine napkins and the signaling light 234 blinks on and off when the tampon rail 400 is out of tampons.

Alternatively, there is another variation of a light which is hardwired to female connectors on the motherboard. The light which shines through the symbol of the tampon and the light shines through the symbol of the feminine napkin on the front door. Therefore, these are two variations where in each case when the apparatus is out of product, the lights blink.

If the sanitary pad column 300 is completely out of sanitary pads 3000, a first magnet 310 affixed to a first weight 320 located at the top of the sanitary pad column 300 engages a signal through a first reed switch 310RS to cause a light 134 to shine on or through front door 20 to show that the sanitary pad column 300 is out of sanitary napkin stock. A second reed switch 410RS is hardwired to motherboard 1000 by wire leads from the second reed switch to female connectors on the motherboard 1000. When the door 20 is closed, the sensor board 130 is located adjacently to the first reed switch 310RS and the sensor board 410RS is located adjacently to the second reed switch 410RS.

If the tampon column 400 is completely out of tampons 4000, a magnet 410 affixed to a second weight 420 located at the top of the tampon column 4000 engages a reed switch 410RS, such that the magnet activate the reed switch 410RS to cause a light 234 to shine on or through the front door 20 to show that the tampon column 4000 is out of tampon stock.

If at least one battery dies, the motherboard 1000 sends a signal to both lights 134 and 234 to have them on steadily and non-blinking to advise the person in charge of the machine to change batteries. Other combinations of lights being steadily on and/or blinking are contemplated to distinguish between a loss of battery power and other operations.

The motherboard 1000 has a computer chip which sends all the signals that control all of the operations as discussed. Programmed into the chip are two time delays wherein the machine cannot be operated until that time has elapsed. Programmed into the computer chip is another time delay wherein if one of the products, either the feminine napkin or the tampons, are dispensed, there is an automatic time delay before any other product is dispensed. If a tampon 4000 is dispensed, then again there is the same delay time before another tampon 4000 is dispensed. This avoids the machine being emptied by someone continuously touching a touch screen to dispense a product. Time delays are programmed into the computer chip. Consequently, other periods of time delay are contemplated and are set in the computer chip.

The configuration of the dispenser apparatus 10 provides a compact and efficient structure. The feminine napkin rail 300 is next to the tampon rail 400 with the motherboard and operating members not located between the two rails. Therefore, the width of the machine 10 is significantly reduced. The package for a feminine napkin is significantly larger than the package for the tampon. Therefore sidewalls and 308 of sanitary napkin rail 300 are much deeper than the sidewalls 407 and 408 of the tampon rail 400.

With the respective longitudinal front walls 330 and 340 of the sanitary napkin rail 300 aligned with the respective longitudinal front walls 430 and 440 of the tampon rail 400, sidewall 450 has sufficient space behind tampon back wall 402 to support the motherboard 1000 on a support plate 194. In another embodiment, the motherboard 1000 is located on the sidewall 450. This enables sanitary napkin rail 300 and tampon rail 400 to be next to each other and not separated by the motherboard 1000 or any other parts or components between them.

In addition, the operating motors and shafts, which provide the force to the sanitary napkin dispensing member and the tampon dispensing member positioned below a respective sanitary napkin rail and tampon rails, and not positioned at a location between the sanitary napkin rail 300 and tampon rail 400, also facilitate the narrower shape of the apparatus.

Through the dispenser apparatus, an individual who is handicapped or has difficulty in even rotating a knob, or having to place coins in slots, easily obtains the product by a simple touch. In addition, there is built into a program in one of the circuit boards a timing sequence that after a product such as a feminine pad is dispensed, the next successive feminine pad cannot be dispensed for a period of such as 2 seconds for the touch sensor. Similarly, if a tampon is dispensed, the next successive tampon cannot be dispensed for a period of time such as 2 seconds. This avoids someone from emptying the machine, either intentionally or inadvertently.

Each column/stack operates independently of the other. The first rail, which retains a column 300 of sanitary pads 3000 has a back wall 302 with transversely extending rear walls respectively attached to transversely attached sidewalls 305 and 306 which in turn are attached to respective vertically attached transversely extending front walls 330 and 340 to create a frame.

With respect to the activation mechanism, and referring to FIGS. 1, 6, 7, 8, and 9, there is a sanitary napkin dispensing system 176 and a tampon dispensing system 178. The sanitary napkin dispensing system 176 includes as illustrated a left motor 160 that is connected to a left drive shaft (not shown) that is integrally affixed to a circular rotating flywheel 164 having a left crank shaft 170 that is connected to circular rotating flywheel 164 at a crank shaft first end 172 and connected to a dispensing member or cradle 179 having first left distribution arm 180L1 at a crank arm second end 174. During operation or after a user touches left touch sensor 130 and the signal is sent to the motherboard to activate left motor 160, battery 2000 powers left motor 160 to rotate left drive shaft (not shown) by three-hundred sixty degrees. Drive shaft (not shown) and integrally affixed circular rotating flywheel 164 rotate in one direction for approximately 360 degrees. The rotation of circular rotating flywheel 164 causes left crank arm 170 to move upwardly 180 degrees to a peak position when drive shaft (not shown) and integrally affixed circular rotating flywheel 164 rotates approximately 180 degrees. This peak position causes first left distribution arm 180L1 illustrated initially having a first left predominantly horizontal wall 182L1 in FIG. 8 to rotate to a forward tilted position having an approximate downwardly sloping angle away from horizontal at an angle of 45 degrees illustrated in FIG. 9. At the peak position, sanitary pad 3000 falls into a distribution tray 500. Then left crank arm 170 moves from peak position back to initial starting position which causes first left predominantly horizontal wall 182L1 of first left distribution arm 180L1 to rotate from an approximate downward angle of 45 degrees to rotate in the opposite direction in a backward rotation by 45 degrees back to the initial starting position of approximately 0 degrees.

Figure 1:
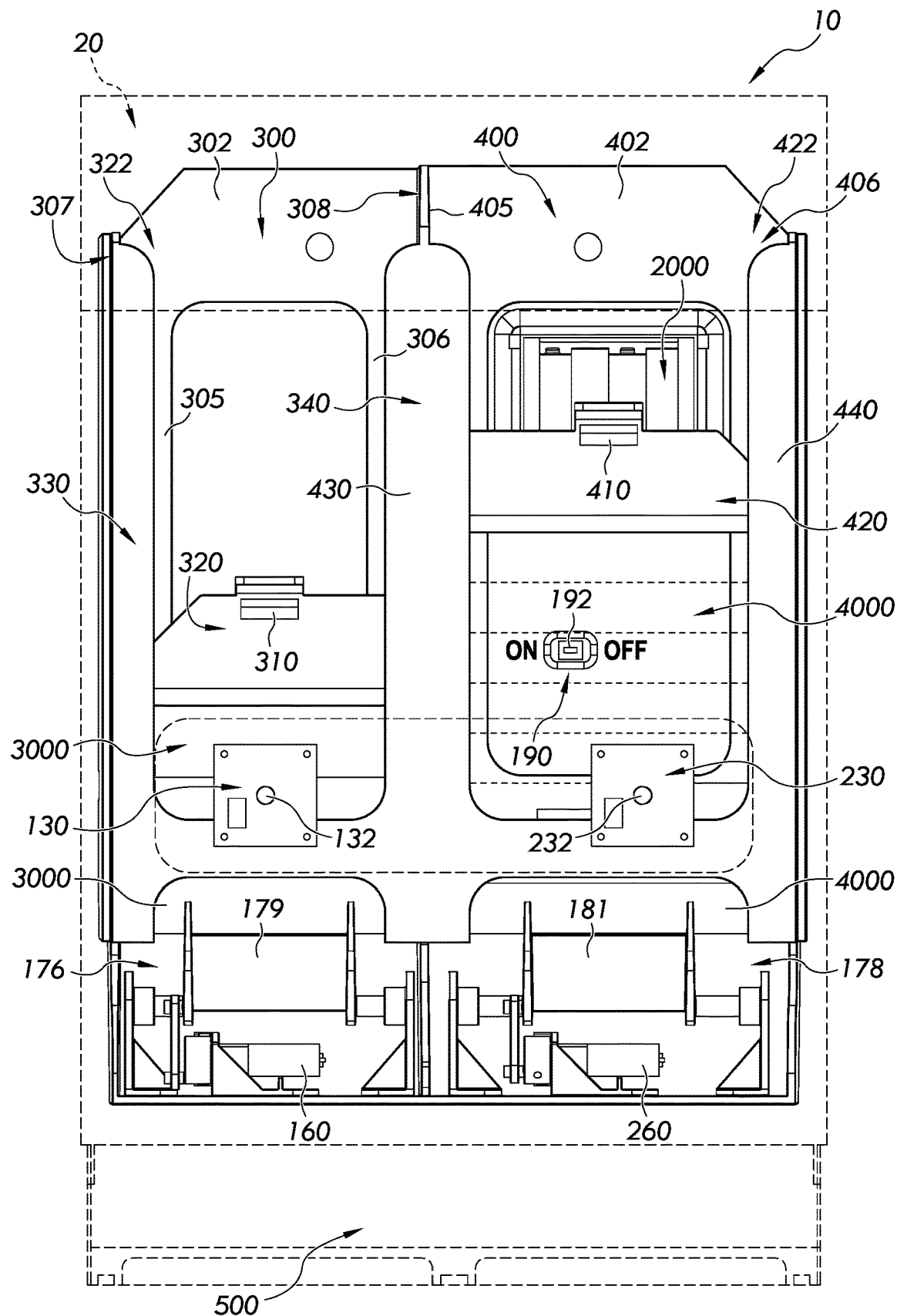
FIG. 1 is an elevational front view a dispenser apparatus in a closed condition and an opening leading to the product retrieval tray.

During operation and when column 300 is retaining sanitary napkins 3000, one of the sanitary napkins is pushed forward and onto dispensing tray 500 (illustrated in FIG. 1). As described herein, the forward position is defined as being directed toward the back wall 70 of the housing 24 and away from a user located in front of the dispenser apparatus 10. When the sanitary napkins are pushed forward, the napkin is directed to a space located between the back wall 70 of the housing 24 and the back wall 302 of the first rail 322. The dispensed sanitary napkin falls through the space and into the dispensing tray 500.

When activated by a user touching the sanitary napkin sensor 130, first left distribution arm 180L1 rotates from an initial condition of flat to a tilted forward condition toward the back wall 70. First left distribution arm 180L1 is directly connected to second left distribution arm 180L2 by left shaft (not shown). The rotation forward and toward the back wall 70 of first left distribution arm 180L1 causes second left distribution arm 180L2 to simultaneously rotate toward the back wall. The left and right distribution arms then rotate in the reverse direction by forty-five (45) degrees until they rotate and return to their initial horizontal condition and the next lowermost sanitary napkin falls onto the sanitary napkin distribution arms.

Also, as a sanitary napkin is dispensed outwardly onto dispensing tray 500, another sanitary napkin moves from an upper position to a lower position and rests on a first left predominantly horizontal wall 182L1 and a second left predominantly horizontal wall 182L2 until a user presses touch sensor 130.

Figure 10:
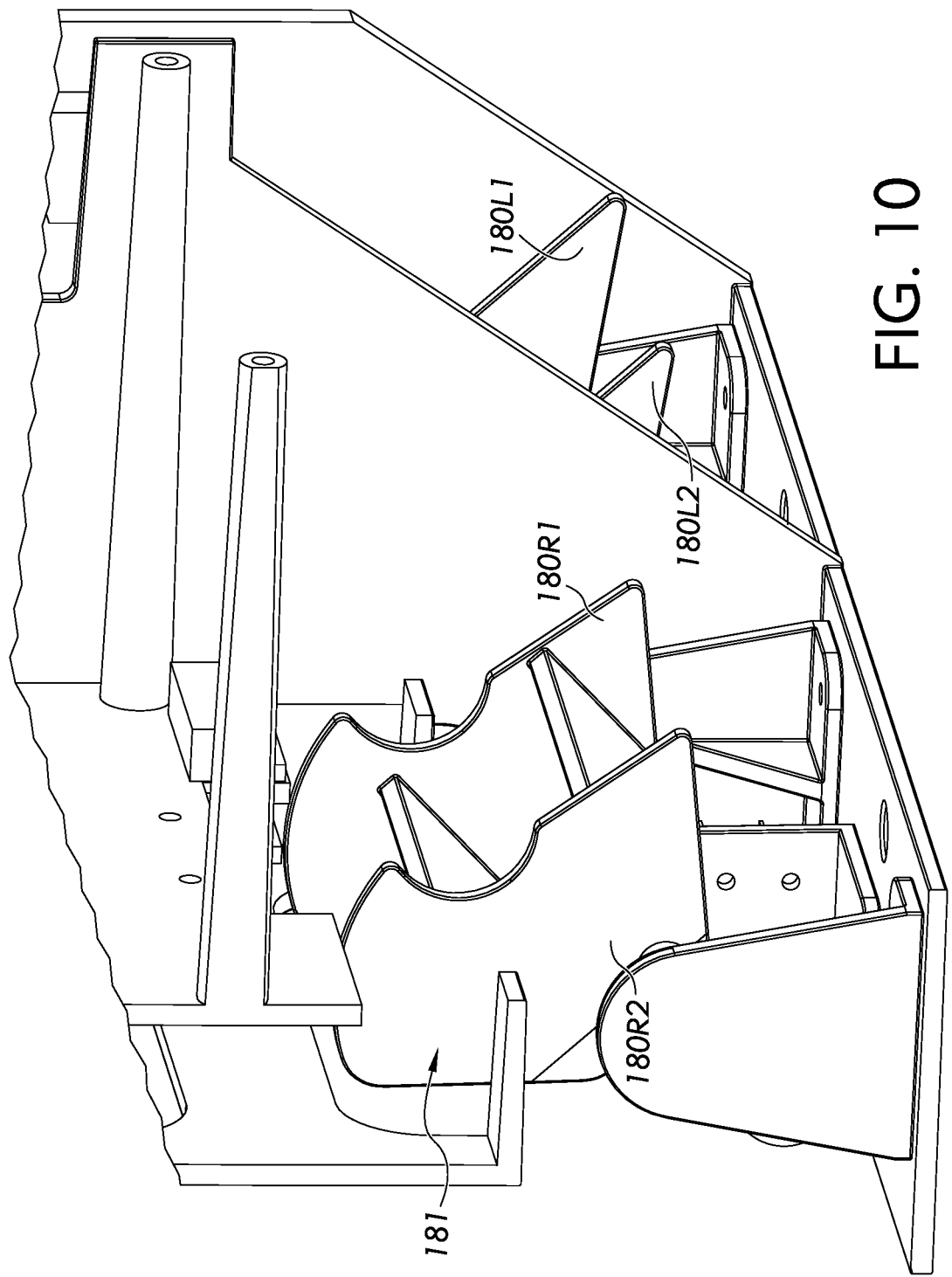
FIG. 10 illustrates a close-up rear view of the dispenser apparatus illustrating both dispensing arms in the initial resting position for the tampon dispenser.
Figure 11:
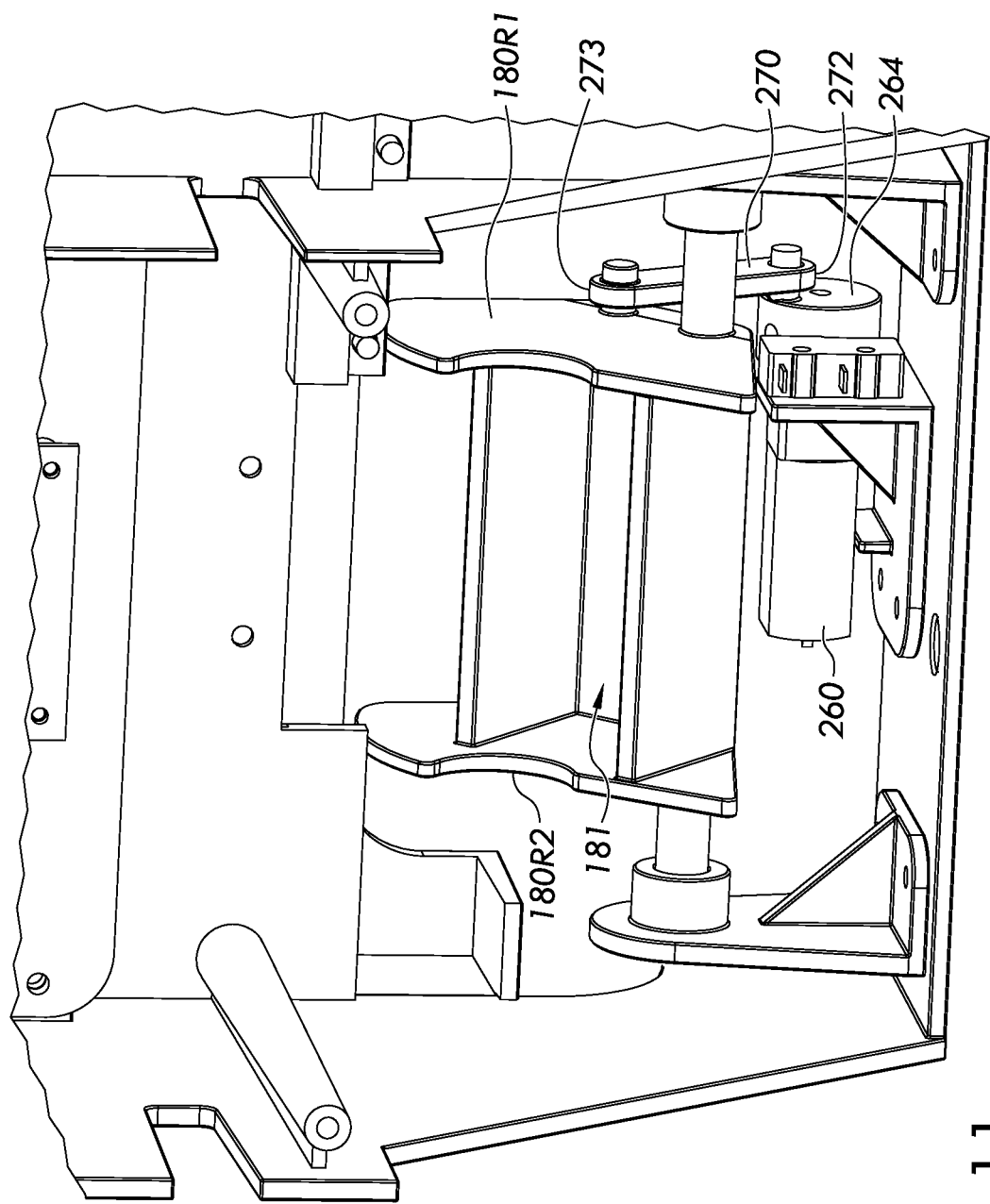
FIG. 11 illustrates a close-up rear view of the dispenser apparatus illustrating both dispensing arms in the forward position for the tampon dispenser.

The operation of the tampon dispensing system to the right of the sanitary napkin dispensing system functions mostly the same. Similar, to previously described sanitary napkin dispensing system, tampon dispensing system has a right motor 260 that is connected to a right drive shaft (not shown) that is integrally affixed to a circular rotating flywheel 264 having a right crank arm 270 that is connected to a right circular rotating flywheel 264 at a right crank arm first end 272 and connected to a dispensing member or cradle 181 having a first right distribution arm 180R1 at a right crank arm second end 273. During operation or after a user touches right touch sensor 230 and the signal is sent to the motherboard 1000 to activate right motor, battery 2000 powers right drive shaft and integrally affixed right circular rotating flywheel to rotate 360 degrees. The rotation of right circular rotating flywheel 264 causes right crank arm 270 to move upwardly 180 degrees to a peak position. When right drive shaft and integrally affixed right circular rotating flywheel rotate approximately 360 degrees, this crank arm 270 peak position causes first right distribution arm 180R1 and second right distribution arm 180R2 illustrated initially having a first right curved wall in FIG. 10 to rotate forward toward the back wall 70 approximately 45 degrees illustrated in FIG. 11. Then right crank arm 270 moves from peak position back to initial starting position which causes first right distribution arm 180R1 and second right distribution arm 180R2 to rotate from a forward position back to an initial resting position at 0 degrees.

Figure 2:
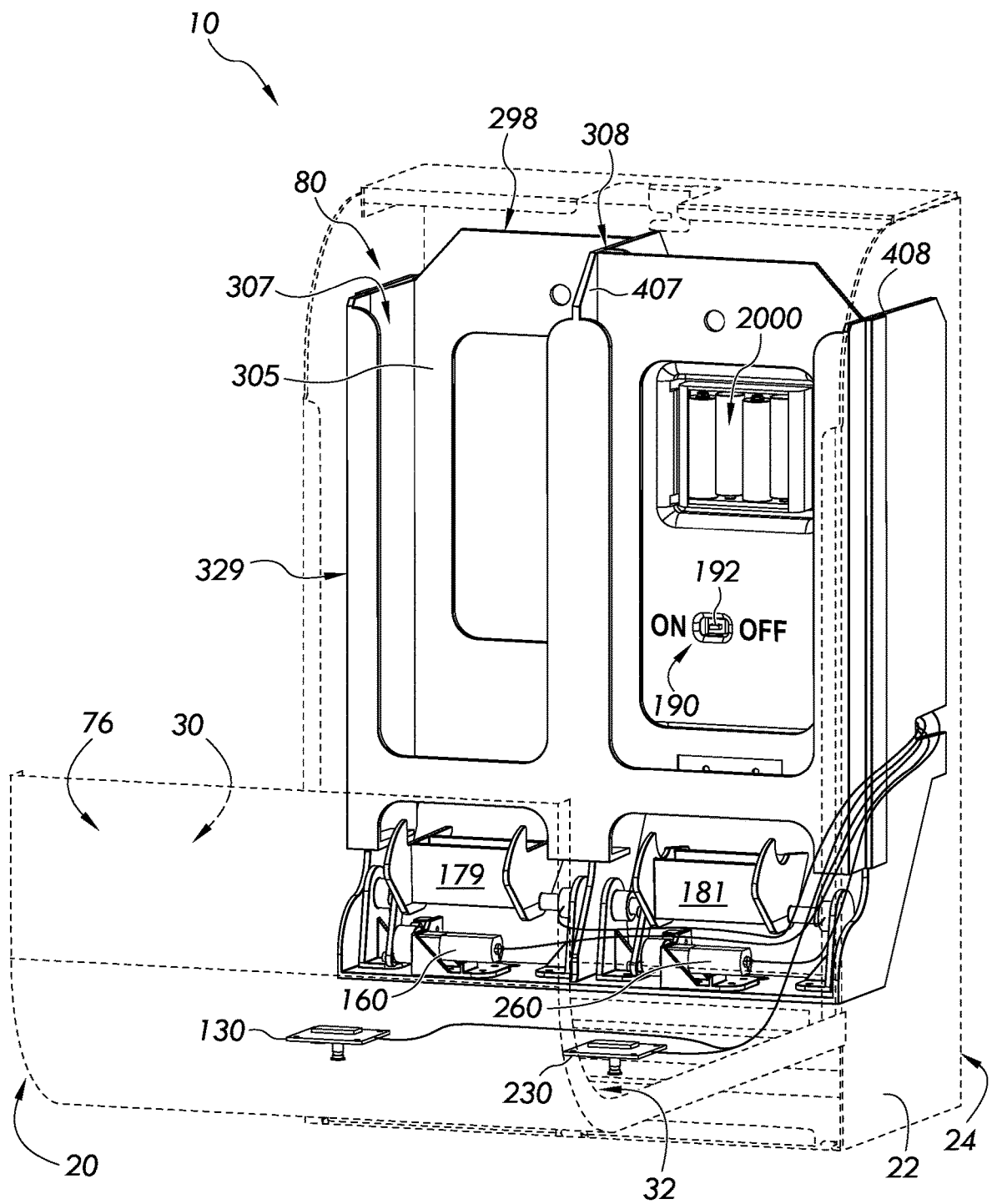
FIG. 2 illustrates an open front door of the dispenser apparatus and illustrating an internal perspective view of the present disclosure.

In another embodiment of the present invention and as illustrated in FIGS. 1 and 2, the dispenser 10 includes a "No-Touch" feature 190 including an on-off switch 192 operatively connected to the computer chip located on the motherboard 1000. In this embodiment, each of the sensors 132 and 232, which are also operatively connected to the motherboard, are configured to operate as both a touch sensor as well as a proximity sensor. The switch 192 includes a first position, an OFF position, and a second position, an ON position, which places the sensors 132 and 232 in one of two modes, a touch mode and a proximity mode. In the OFF position, a touch is required by the sensors for the sensors to be activated. In the ON position or proximity mode, the sensors act as proximity sensors. In another embodiment, the modes of the switch in the ON and OFF positions are reversed. When acting as a proximity sensor, a touch by a user is not necessary to activate the sensor. In the proximity mode the sensors are each capacitive proximity sensors that change states in the presence of a person's hand, for instance. Inductive sensors and other types of proximity sensors are contemplated. Touching the sensor is not necessary in the proximity mode. The computer chip is programmed with a predetermined sensing range that establishes a sensing distance required to activate the sensors. This sensing distance is adjustable by programming the computer program used by the computer chip.

The power pack 2000 is supported by the support plate 194 that is connected to and forms part of the back wall 402 of the front module 398. The back wall 402 includes an opening 196 to which the plate 194 is oriented to expose the batteries in the power pack 2000 for replacement when needed. The batteries are located in a recess of the plate 194 though an aperture. The support plate includes a receptacle 195 having a cavity configured to receive the batteries. In one embodiment, the receptacle is a part separate from the support plate 194 and coupled thereto. In another embodiment, the support plate is a single unitary part formed to include the cavity.

Through the dispenser apparatus, an individual who is handicapped or has difficulty in even rotating a knob, or having to place coins in slots, easily obtains the product by a simply touching the touch sensor. In the alternative, when the dispenser is operating in the proximity mode, a touch is not required and only proximity, of a person's hand for instance, is required.

Insofar as the description above and the accompanying drawings disclose any additional subject matter that is not within the scope of the claims, the disclosed inventions are not dedicated to the public and the right to the one or more applications to claim such additional inventions is reserved.

An apparatus for dispensing feminine napkins and tampons includes a container having a front door or front cover, a back wall and a pair of oppositely disposed sidewalls, a top wall and a bottom wall which surround an interior chamber, wherein the front door is rotatably attached to one of the sidewalls or to the bottom wall and the top cover is rotatably attached to the back wall. A first sanitary napkin rail includes a back wall having a first longitudinal back wall leading to a first longitudinal side wall leading to a first longitudinal front wall and a second longitudinal back wall leading to a second longitudinal side wall leading to a second longitudinal front wall and configured to retain a column of individual sanitary napkins. A first top weight bearing platform includes a first magnet resting on the uppermost sanitary napkin. A first tampon rail includes a back wall having a first longitudinal back wall leading to a first longitudinal sidewall leading to a first longitudinal front wall and a second longitudinal back wall leading to a second longitudinal side wall leading to a second longitudinal front wall and configured to retain a column of individual tampons. A second top weight bearing platform includes a second magnet resting on the uppermost tampon.

The first longitudinal sidewall of the sanitary napkin rail is next to the second longitudinal sidewall of the tampon rail. The first longitudinal sidewall and the second longitudinal side wall in one embodiment is a shared sidewall. The first and second sidewalls of the sanitary napkin rail are deeper than the first and second longitudinal sidewalls of the tampon rail. The first and second longitudinal front wall of the sanitary napkin rail is aligned with the first and second front wall of the tampon rail.

A motherboard includes a computer chip which sends the signals that control the operations including two programmed time delays which create a delay in dispensing a second sanitary napkin after a first sanitary napkin has been dispensed and a time delay in dispensing a second tampon after a first tampon has been dispensed. The motherboard is affixed to the first sidewall of the sanitary napkin rail or to the back wall of the tampon rail at a location behind the tampon rail. The motherboard includes a multiplicity of female connectors. A first feminine napkin touch sensor is affixed to a back surface of the front door and is hardwired by a four ribbon wire to respective female connectors on the motherboard. Two wire leads are hardwired from two respective female connectors on the motherboard to a source of power. The motherboard is also hardwired by a portion of a four wire ribbon with two wire leads from female connectors on the motherboard to first micro limit switch and two wire leads from female connectors on the motherboard to a first or left driver motor. The left driver motor is connected to a first shaft.

A first tampon touch sensor is affixed to a back surface of the front door and is hardwired by a four ribbon wire to respective female connectors on the motherboard. The motherboard is also hardwired by a portion of a four wire ribbon with two wire leads from female connectors on the motherboard to a second micro limit switch and by two wire leads from female connectors on the motherboard to a second or right driver motor. The right drive motor is connected to a second shaft. A left reed switch is hardwired by two wire leads to connectors on the motherboard. A right reed switch is hardwired by two wire leads to connectors on the motherboard. A left limit switch is hardwired by two wire leads to connectors on the motherboard. A right limit switch is hardwired by two wire leads to connectors on the motherboard.

When the front cover is touched at the location of the sanitary napkin sensor, a signal is sent to the motherboard to activate the left motor. The source of power powers the left motor to rotate the left drive shaft and integrally affixed rotating flywheel connected to a crank arm which moves in a generally vertical direction and connected to dispensing arms supporting a lowermost sanitary napkin. The rotating cradle rotates approximately forty-five degrees in the direction toward the back wall to cause the feminine napkin to fall into a retrieval tray. The cradle then rotates in the direction toward the front wall by approximately forty-five degrees back to its starting position to return the cradle to its initial position and retains a successive sanitary napkin. A time delay prevents a second sanitary napkin to be dispensed until the time delay has expired. Said time delay prevents a second sanitary napkin to be dispensed until the time delay has passed. When the front cover is touched at the location of the tampon sensor, a signal is sent to the motherboard to activate the right motor. The source of power powers the right motor to rotate the right drive shaft. The integrally affixed rotating flywheel connected to a crank moves in a vertical direction and is connected to cradle supporting a lowermost tampon.

The cradle rotates approximately forty-five degrees in the forward direction toward the back wall to cause the feminine napkin to fall into a retrieval tray. The cradle then rotates in the backward direction toward the front wall by approximately forty-five degrees back to its starting position to return the cradle to its initial position and to retain a successive tampon wherein the time delay prevents a second tampon to be dispensed until the time delay has passed. If the sanitary napkin column is completely out of sanitary napkins, the magnet affixed to the first weight at the top of the sanitary napkin column engages the left reed switch to cause a light to shine on or through the front door to show that the sanitary napkin column is out of tampon stock. If the tampon column is completely out of tampons, the magnet affixed to the second weight at the top of the tampon column engages the right reed switch to cause a light to shine on or through the front door to show that the tampon column is out of tampon stock.

Of course the present invention is not intended to be restricted to any particular form or arrangement, or any specific embodiment, or any specific use, disclosed herein, since the same may be modified in various particulars or relations without departing from the spirit or scope of the claimed invention herein above shown and described of which the apparatus or method shown is intended only for illustration and disclosure of an operative embodiment and not to show all of the various forms or modifications in which this invention might be embodied or operated.

What is claimed is:

1. A dispensing apparatus for dispensing hygiene products, the apparatus comprising:
   a first hygiene product rail having a first sidewall, the first hygiene product rail to hold first hygiene products;
   a second hygiene product rail having a second sidewall, the second hygiene product rail to hold second hygiene products;
   a motherboard;
   a first hygiene product sensor operatively connected to the motherboard, wherein activation of the first hygiene product sensor dispenses first hygiene products from the first hygiene product rail; and
   a second hygiene product sensor operatively connected to the motherboard, wherein activation of the second hygiene product sensor dispenses second hygiene products from the second hygiene product rail.

2. The dispensing apparatus of claim 1 further comprising a door having an open position, a closed position, a front surface and a back surface, wherein the first hygiene product sensor and the second hygiene product sensor are each operatively connected to the back surface the door.

3. The dispensing apparatus of claim 2 wherein when the door is in the closed position the first hygiene product sensor is located adjacently to the first hygiene product rail and the second hygiene product sensor is located adjacently to the second hygiene product rail.

4. The dispensing apparatus of claim 3 further comprising:
   a first cradle and a first motor disposed beneath the first hygiene product rail, the first motor connected to a first crank arm to dispense the first hygiene product from the first cradle; and
   a second cradle and a second motor disposed beneath the second hygiene product rail, the second motor connected to a second crank arm to dispense the second hygiene product from the second cradle.

5. The dispensing apparatus of claim 3 wherein the mother board includes a computer chip operatively connected the first and second hygiene product sensors.

6. The dispensing apparatus of claim 1 wherein the first and second hygiene product sensors include one of a touch sensor or a proximity sensor.

7. The dispensing apparatus of claim 1 wherein the first and second hygiene product sensors include a dual purpose sensor to respond to a touch of a user or a proximity of a user.

8. The dispensing apparatus of claim 1 further comprising a selection switch operatively connected to the mother board, wherein the selection switch includes a first position to select a touch mode and a second positon to select a proximity mode, wherein in the touch mode the first and second hygiene product sensors are activated by the touch of the user and wherein in the second mode the first and second hygiene product sensors are activated by the proximity of the user without the touch being required.

9. The dispensing apparatus of claim 1 further comprising a power connection wherein the power connection is configured to connect to a battery or a building power system.

10. A hygiene product dispensing apparatus for dispensing hygiene products comprising:
    a first hygiene product structure having a first sidewall, the first hygiene product structure to hold first hygiene products;
    a second hygiene product structure having a second sidewall, the second hygiene product structure to hold second hygiene products;
    a computer chip;
    a first hygiene product sensor operatively connected to the computer chip, wherein activation of the first hygiene product sensor dispenses first hygiene products from the first hygiene product structure;
    a second hygiene product sensor operatively connected to the computer chip, wherein activation of the second hygiene product sensor dispenses second hygiene products from the second hygiene product structure; and
    wherein the computer chip is programmed to include a time delay and if one of the first hygiene product or the second hygiene product products is dispensed, the computer chip provides an automatic time delay before the other of the first hygiene product or the second hygiene product is dispensed.

11. The hygiene product dispensing apparatus of claim 10 further comprising a selection switch operatively connected to the computer chip, wherein the selection switch includes a first position to select a touch mode and a second positon to select a proximity mode, wherein in the touch mode the first and second hygiene product sensors are activated by the touch of the user and wherein in the second mode the first and second hygiene product sensors are activated by the proximity of the user without the touch being required.

12. The hygiene product dispensing apparatus of claim 11 further comprising a first dispensing member located below the first hygiene product structure to dispense the first hygiene product and a second dispensing member located below the second hygiene product structure to dispense a second hygiene product.

13. The hygiene product dispensing apparatus of claim 12 wherein actuation of the first hygiene product sensor causes the first dispensing member to dispense one of the first hygiene products.

14. The hygiene product dispensing apparatus of claim 13 wherein actuation of the second hygiene product sensor causes the second dispensing member to dispense one of the second hygiene products.

15. The hygiene product dispensing apparatus of claim 14 further comprising a door having an open position, and a closed position, wherein the first hygiene product sensor and the second hygiene product sensor are each operatively connected to the door.

16. A method of dispensing a first hygiene product and a second hygiene product from a dispensing apparatus comprising:
    providing a first hygiene product rail to hold a first column of a plurality of the first hygiene products;
    providing a second hygiene product rail to hold a second column of a plurality of the second hygiene products;
    dispensing one of the plurality of first hygiene products from the first column in response to activation of a first sensor, wherein the response is based on a condition of a switch having a touch activation mode or a proximity activation mode;
    dispensing one of the second hygiene products from the second column in response to activation of a second sensor, wherein the response is based on the condition of the switch having the touch activation mode or the proximity activation mode; and
    illuminating a light if one of the first column or the second column is out of the first hygiene product or second hygiene product.

17. The method of claim 16 wherein the illuminating step includes illuminating a first light if the first column is out of the first hygiene product.

18. The method of claim 17 wherein the illuminating step includes illuminating a second light if the second column is out of second hygiene product.

19. The method of claim 16 further providing a power connection wherein the power connection is configured to connect to one of both of battery or building power system.

20. The method of claim 16 further comprising illuminating the light or another light if the power connection does not receive power.

* * * * *